(12) United States Patent
Vayser et al.

(10) Patent No.: US 10,226,555 B2
(45) Date of Patent: Mar. 12, 2019

(54) THERMALLY CONTROLLED ILLUMINATION DEVICES

(71) Applicant: Invuity, Inc., San Francisco, CA (US)

(72) Inventors: Alex Vayser, Mission Viejo, CA (US); Gaston Tudury, San Francisco, CA (US); Fernando Erismann, New York, NY (US)

(73) Assignee: Invuity, Inc., San Francisco, CA (US)

( * ) Notice: Subject to any disclaimer, the term of this patent is extended or adjusted under 35 U.S.C. 154(b) by 0 days.

(21) Appl. No.: 14/487,645

(22) Filed: Sep. 16, 2014

(65) Prior Publication Data
US 2015/0080666 A1    Mar. 19, 2015

Related U.S. Application Data

(60) Provisional application No. 61/878,395, filed on Sep. 16, 2013.

(51) Int. Cl.
*A61B 1/06* (2006.01)
*A61M 1/00* (2006.01)
(Continued)

(52) U.S. Cl.
CPC .............. *A61M 1/008* (2013.01); *A61B 17/02* (2013.01); *A61B 90/30* (2016.02);
(Continued)

(58) Field of Classification Search
CPC ........ A61B 1/06; A61B 1/0607; A61B 1/0615
See application file for complete search history.

(56) References Cited

U.S. PATENT DOCUMENTS

| | | | | |
|---|---|---|---|---|
| 6,080,105 A | * | 6/2000 | Spears | ..................... A61B 1/06 600/212 |
| 7,371,213 B2 | * | 5/2008 | Hestad | ................... A61B 17/02 600/245 |

(Continued)

FOREIGN PATENT DOCUMENTS

| | | |
|---|---|---|
| JP | 2012500043 A | 1/2012 |
| WO | WO-2013044151 A1 | 3/2013 |

OTHER PUBLICATIONS

International search report and written opinion dated Dec. 18, 2014 for PCT Application No. US2014/055910.
European search report and search opinion dated Aug. 26, 2016 for EP Application No. 14845357.4.

*Primary Examiner* — Julianna N Harvey
(74) *Attorney, Agent, or Firm* — McDonnell Boehnen Hulbert & Berghoff LLP

(57) ABSTRACT

An illumination element such as an optical waveguide for illuminating a surgical field in a patient has a light input section, a light transmitting section, and a light output section. The light input section is optically coupled to a proximal section of the light transmitting section and inputs light into the illumination element. The light transmitting section transmits the light preferably by total internal reflection or by other transmission means. The light output section is adjacent a distal section of the light transmitting section which has a light extraction area from which the light exits with an energy density. The light extraction area is large enough to maintain the energy density at a level that prevents melting of the illumination element or burning of the patient, and the light extraction area has a profile that does not interfere with access to the surgical field.

22 Claims, 10 Drawing Sheets

(51) Int. Cl.
  *A61B 17/02*     (2006.01)
  *A61B 90/30*     (2016.01)
  *A61B 17/00*     (2006.01)

(52) U.S. Cl.
  CPC .............. *A61B 2017/00296* (2013.01); *A61B 2090/306* (2016.02); *A61B 2217/005* (2013.01)

(56) References Cited

U.S. PATENT DOCUMENTS

| | | |
|---|---|---|
| 8,088,066 B2 | 1/2012 | Grey et al. |
| 2002/0009275 A1 | 1/2002 | Williams et al. |
| 2002/0103419 A1* | 8/2002 | Christopher ....... A61B 1/00073 600/156 |
| 2005/0165283 A1 | 7/2005 | Hestad et al. |
| 2007/0189701 A1* | 8/2007 | Chakmakjian ....... G02B 6/0028 385/146 |
| 2009/0054900 A1 | 2/2009 | Rabiner et al. |
| 2009/0112068 A1* | 4/2009 | Grey ...................... A61B 17/02 600/212 |
| 2010/0030033 A1* | 2/2010 | Farley ...................... A61B 1/07 600/249 |
| 2010/0041955 A1 | 2/2010 | Grey et al. |
| 2013/0012783 A1* | 1/2013 | Vayser ............... A61B 1/00135 600/249 |
| 2013/0079598 A1* | 3/2013 | Auld .................. A61B 19/5202 600/249 |
| 2013/0245613 A1* | 9/2013 | Salehi .................. A61C 17/043 604/540 |

* cited by examiner

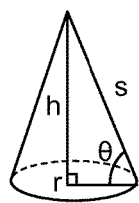
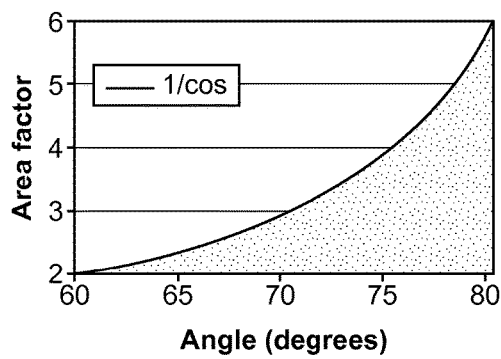
FIG. 17A
FIG. 17B
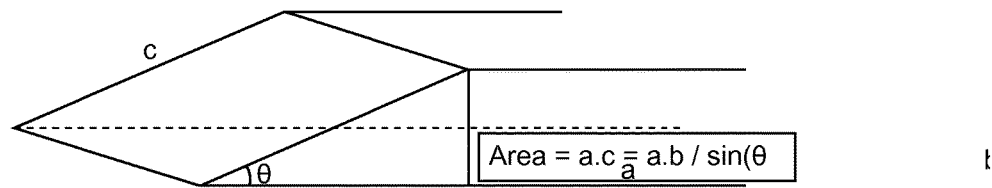
FIG. 18A
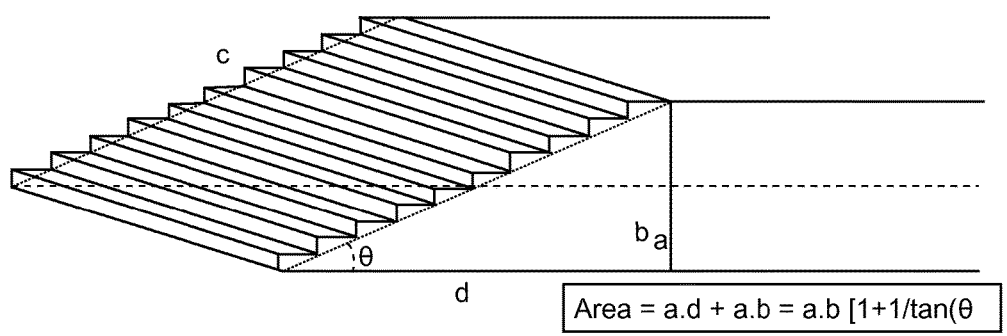
FIG. 18B

THERMALLY CONTROLLED ILLUMINATION DEVICES

CROSS-REFERENCE

The present application is a non-provisional of, and claims the benefit of U.S. Provisional Patent Application No. 61/878,395 filed Sep. 16, 2013; the entire contents of which are incorporated herein by reference.

BACKGROUND OF THE INVENTION

1. Field of the Invention

The present invention generally relates to medical devices and methods, and more particularly relates to illuminated surgical instruments such as illuminated surgical retractors and handheld instruments such as illuminated suction devices. One of skill in the art will appreciate that these examples are not intended to be limiting and that other illuminated instruments or tools are also contemplated.

There are various surgical devices in the market that provide illumination to a surgical field. A number of these devices are either manufactured from a bundle of fibers or a single fiber. In the operating room, modern light sources are used to produce a tremendous amount of illumination intensity. This energy is coupled into these illumination products, which transmit the light over a distance and then the energy is output onto the surgical surface.

In certain circumstances, these devices can create a thermal danger to the patient, the user, or the equipment being used. When all the optical energy from a fiber bundle is focused on a patient, tissue can dry out, and the heat generated can also result in burns. Surgical drapes have been reported to melt and catch on fire in the operating room. During surgical procedures, blood, other debris, or surgical drapes may obstruct the device and block light output. Obstructing light creates several issues. The first is reduction of illumination on the field, thus minimizing the visual acuity of the task. This obviously can affect the efficiency of the procedure. A more critical issue however is thermal buildup on the section of the illumination device which is obstructed. Since the light cannot exit, it converts to heat as it is blocked. Blood, for example, coagulates at an average temperature of 40° C., so as it coagulates on the surface of the illumination device it will block light output minimizing the amount of light exiting the device. The increased energy density will also further heat up the device. Fiber bundles are often fabricated from glass which may not be affected by this, but adhesives used in the fiber bundle assembly may be damaged from the heat, and when the fiber bundles are fabricated from polymers, the fibers may heat up and melt or exceed the glass transition temperature and deform. Therefore it would be desirable to provide illuminated surgical instruments that are able to control heat generated so as to avoid damaging the illuminated surgical instrument, as well as avoiding harming the patient or operator. In the example of the surgical drape, if the drape is obstructing the illumination element, the energy density on the drape is much higher for several reasons. As mentioned earlier the illumination element heats up if the drape is actually touching the illumination element. The other reason is that if the drape is very close to the illumination element and there is air space, the energy density of light being absorbed by the drape is so high that it will melt the drape when compared to a drape that is disposed further away from the illumination element and the light is dispersed over a larger area on the drape.

Therefore, it would be desirable to provide a device that has a low energy density output. Energy density may be controlled by increasing the surface area from which the light is delivered, thereby reducing the heat generated. However, an increase in surface area may increase the overall profile of the surgical device. This may be undesirable because a larger surgical device may occupy too much space in the surgical field, thereby requiring a larger incision which is undesirable. Thus, with ever decreasing surgical incision sizes, it would also be advantageous to provide an illuminated surgical instrument with a low profile so as to avoid obstructing the surgical field.

At least some of these objectives will be satisfied by the devices and methods disclosed below.

2. Description of the Background Art

Illuminated surgical instruments may include illumination elements such as fiber optics, optical waveguides, or other means for providing the light. Optical waveguides and fiber optics are well known in the art.

SUMMARY OF THE INVENTION

The present invention generally relates to medical devices and methods, and more particularly relates to medical and surgical instruments that can illuminate a surgical field. Even more particularly, such illuminated surgical and medical instruments are designed to control and manage their thermal properties during use so as to minimize or prevent melting or other damage to the instrument, the surgical field, and harm to the patient or operator.

In a first aspect of the present invention, an illumination element for illuminating a surgical field in a patient may comprise a light input section, a light transmitting section, and light output section. The light input section is for inputting light into the illumination element, and the light transmitting section transmits light therethrough, preferably by total internal reflection or by other means such as by using coatings on the illumination element. The light input section is optically coupled to a proximal section of the light transmitting section. The light output section is adjacent a distal section of the light transmitting section, and comprises a light extraction area with light exiting the light output section with an energy density. The light extraction area is large enough to maintain the energy density at a level that prevents melting or other damage of the illumination element or burning of the patient or operator, and the light extraction area has a low profile configured to avoid obstructing access to the surgical field and visualization thereof.

The light output section may be tapered, either flat or conically tapered, and the light output section may comprise an upper surface and a flat planer lower surface. The upper surface may be angled relative to the flat planer lower surface. The upper surface may form an angle of 30 degrees or less relative to the flat planar lower surface. In alternative embodiments, the upper surface or the lower surface may be curved.

The light input section may have a cross-sectional area, and the extraction area may be at least twice the input cross-sectional area. The light extraction area may be balanced so as to provide uniform light output therefrom. Balancing may be accomplished with light extraction surface features such as lenslets, prisms, stair steps, or other features which help control and direct the extracted light. The light input cross-sectional area may be in a plane that is perpendicular or otherwise transverse to the plane of the light extraction area.

The illumination element may be an optical waveguide and may further comprise cladding disposed over at least a section of the light input section, light transmitting section, or the output section. The cladding may have an index of refraction in the range from about 1 to about 1.5.

The illumination element or optical waveguide may further comprise a surgical instrument coupled to the light input section, the light transmitting section, or the light output section. The surgical instrument may comprise a suction tube or a surgical retractor blade. The suction tube or the surgical instrument may comprise interchangeably sized tips.

The illumination element may comprise an optical waveguide, and light input into the illumination element may be transmitted through the transmitting section by total internal reflection, or by other means for transmission.

In another aspect of the present invention, a method for illuminating a surgical field in a patient comprises providing an illumination element such as an optical waveguide having a light input section, a light transmitting section, and a light output section, and inputting light from an external source into the illumination element or the optical waveguide via the light input section. The method also comprises transmitting the light through the light transmitting section, and this may be accomplished via total internal reflection or another light transmission means, and extracting the light from the light output section. The method also comprises maintaining energy density of the light extracted from the light output section at a level that prevents melting of the illumination element which may be an optical waveguide or burning of the patient or operator, and illuminating the surgical field with the extracted light.

The method may comprise advancing the illumination element or optical waveguide toward the surgical field without obstructing the surgical field. Maintaining the energy density may comprise providing the input section with a cross-sectional area, and providing the light output section with a light extraction area, wherein the light extraction area is at least twice the input section cross-sectional area. The cross-sectional area of the input section may be in a plane that is perpendicular or otherwise transverse to the plane in which the light extraction area is disposed.

The method may further comprise balancing the extracted light so as to provide uniform illumination of the surgical field. This may be accomplished by providing extraction surface features on the illumination element such as lenslets, prisms, or stair steps which help control and direct the extracted light. The method may also comprise providing a suction tube or a surgical instrument coupled to the light input section, the light transmitting section, or the light output section of the illumination element or optical waveguide. The method may further comprise interchanging interchangeable instrument tips with either the suction tube or the surgical instrument.

In some embodiments, the illumination element comprises an optical waveguide and light is transmitted through the transmitting section via total internal reflection or by other transmission means.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 17A-17B illustrate the relationship between a conical taper angle and the surface area.

FIGS. 18A-18B illustrate how stair steps create additional surface area relative to a tapered surface.

DETAILED DESCRIPTION OF THE INVENTION

Specific embodiments of the disclosed device and method will now be described with reference to the drawings. Nothing in this detailed description is intended to imply that any particular component, feature, or step is essential to the invention.

Figure 1:
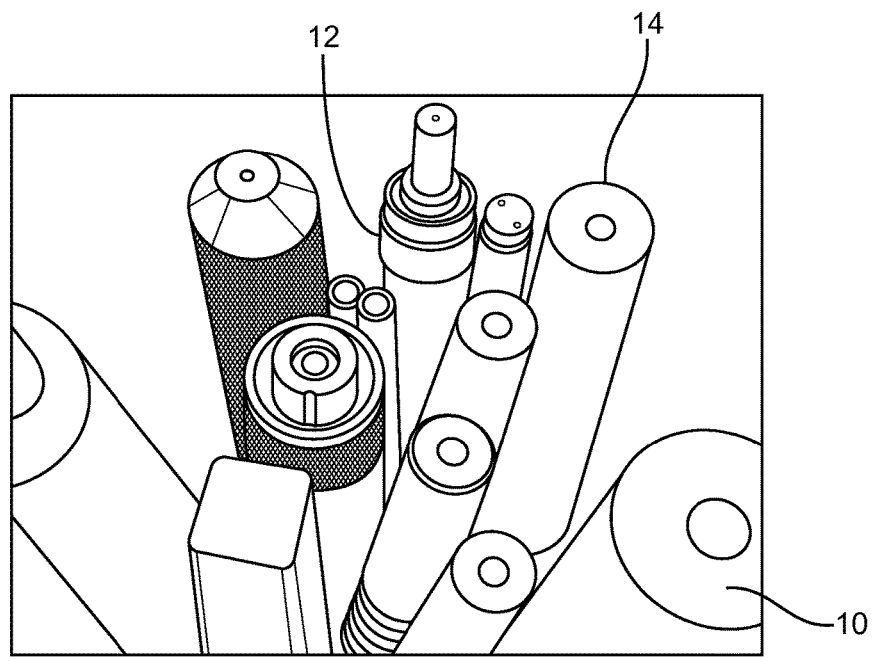
FIG. 1 illustrates typical fiber optic cables.

FIG. 1 illustrates typical fiber optic cables 10 which are often constructed in a barrel type connector 12 and have distal tips are circular and flat 14. The reason they are cut flat is because when they are assembled, they are cut and polished. The maximum angle one can polish the fiber bundle depends on how much light will come out of the fiber, and this in turn depends on the critical angle, which may be determined based on total internal reflection calculations. Based on the material of the fiber and any air interface, a typical angle is approximately 6 degrees. The angle may be greater than 6 degrees, but efficiency starts to drop.

Fiber optic cables are often connected to external light sources, such as a 300 Watt xenon light source, which exhibits high power output. When the tip of the fiber is absolutely clean or unobstructed, the temperature of the tip remains at safe levels, however when the tip of the fiber optic cable is obstructed with absorbing media such as debris, blood or fluids or even blocked by a surgical drape or a patient's skin, the illumination energy density quickly converts to heat and the tip heats up. The temperature can rise to over 150° C. This temperature is high enough to cause a burn on a patient or the operator, or melt a surgical drape or even result in a fire. Since blood coagulates at a much lower temperature, it will "bake" on the tip greatly reducing the output. This causes less visibility to the surgical procedure for the surgeon thus potentially creating risk. Additionally, as previously mentioned even if the illuminator is not blocked and there is an air gap, absorption by a drape or skin can still cause damage.

Another issue that the increased temperature can cause is damage to the illuminator. If the illuminator is made of glass fibers, it is unlikely that they will get damaged as the deformation temperature of glass is very high, however if the fiber is formed from plastic fibers, they can melt or deform. Also, any adhesives or polymer components used in the adjacent area may also melt or be damaged by the heat, regardless of whether the illuminator is glass or plastic.

Therefore, it would be desirable to provide illuminated instruments and devices that are better at controlling heat in order to avoid damage to the device or harming the patient or the operator. Such a device preferably maintains the power output while minimizing energy density. One solution is to increase the light output or extraction area. Energy density may be minimized by increasing the extraction area. However, an increase in extraction area can increase the instrument profile which can obstruct the surgical field. Therefore, the energy density is preferably minimized by increasing extraction area, while maintaining a low profile on the device, while at the same time taking into account the thermal conductivity of the device as well as its melting characteristics.

Figure 15:
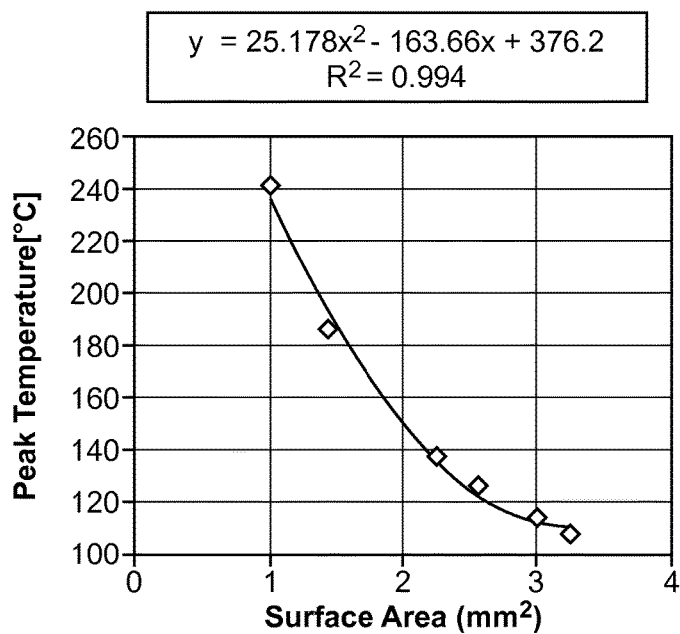
FIG. 15 illustrates the relationship between temperature and surface area in an illumination element.

To address this, one has to create a large output area that minimizes the thermal/energy density across that surface without compromising practicality of the device in surgical applications where it may be too obtrusive. FIG. 15 illustrates the relationship between peak device temperature and surface area in one particular embodiment of an illumination element (also referred to herein as an illuminator). Clearly, temperature decreases with increasing surface area, assuming there is a uniform light output. In particular, there is a significant decrease in temperature for a doubling of the surface area. This graph was generated with a cyclo olefin polymer (COP) waveguide with the surface covered by a 1 W thermal load. In another embodiment, with a large area for delivery of light, if 80% of the light is extracted from only 10% of the device area, this theory may not apply.

Figure 2:
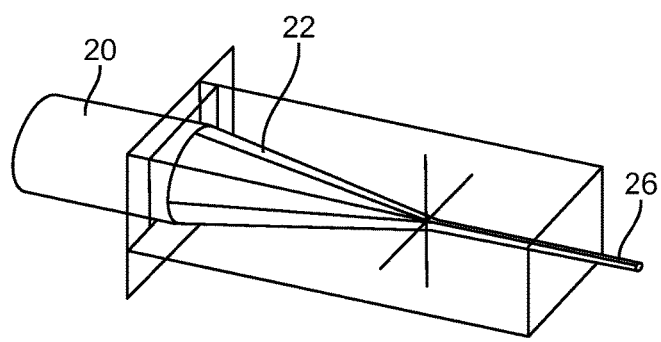
FIG. 2 illustrates a fiber optic with a tapered tip.

FIG. 2 illustrates a fiber bundle 26 having a plurality of flat tapered surfaces disposed around the circumference of the distal tapered region 22 so that the output end of the fiber bundle 20 has a larger output surface area than if the light simply exited the distal-most face of the fiber bundle. This spreads the output over a larger area, thereby keeping energy density lower and preventing overheating. However, this embodiment may not be ideal since the large profile of the bundle 20 may be too obstructive in a surgical field. This embodiment may be fabricated by polishing an outer surface of each fiber on the outer circumference of the bundle. Each outer surface may be polished into a flat planar region. The fibers in the center of the bundle may retain their preferably round configuration.

In order to provide an illumination element such as an optical waveguide that controls heat and provides a suitable profile, the present inventors disclose herein several exemplary embodiments of optical waveguides. Preferably, they may be fabricated using any suitable optical material, such as acrylic, polycarbonate, cyclo olefin polymer (COP), cyclo olefin copolymer (COC), or other materials used in the art. The optical waveguide is preferably coupled to the end of a fiber optic bundle (either releasably attached, fixedly attached (e.g. by bonding), or otherwise coupled thereto). Light is introduced into the optical waveguide from the fiber optic bundle and the light is then preferably transmitted along the waveguide by total internal reflection or by other light transmission principles (e.g. coatings), and the light is then extracted and delivered from a large area of the optical waveguide. The optical waveguide is preferably not a fiber optic. The optical waveguide may be a single unitary component that is preferably injection molded from a homogenous material. The optical waveguide preferably minimizes profile, reduces energy density and extracts light uniformly across the surface of the waveguide.

Figure 3:
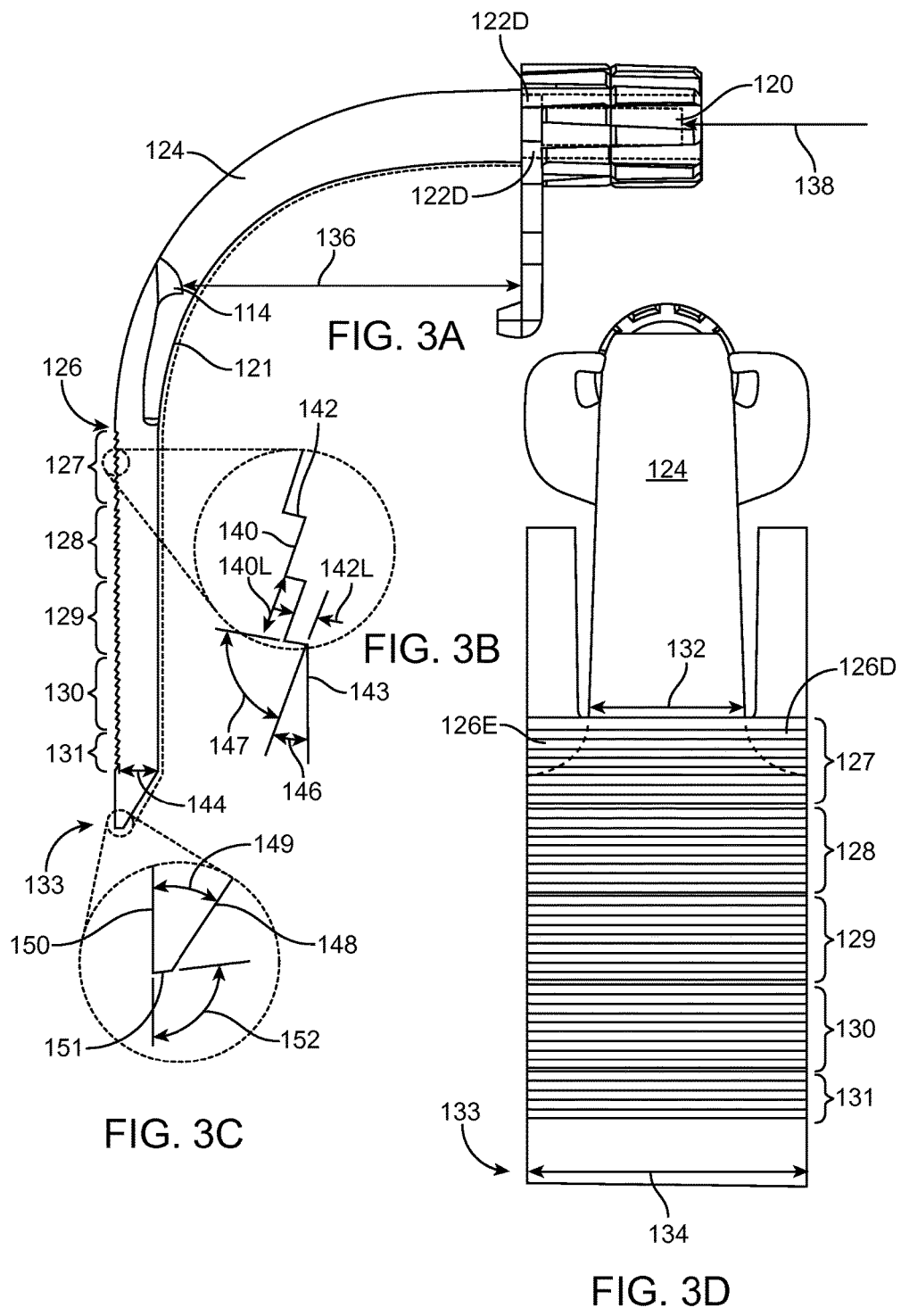
FIGS. 3A-3D illustrate an exemplary embodiment of an illumination element.

To achieve these goals, the extraction area is preferably at least twice the cross-sectional area of the input source for a non-tapered extraction area. The light input section of the illumination element such as an optical waveguide typically matches the cross-sectional area of the input source, therefore, the ratio of the extraction area to the cross-sectional area of the light input section is similarly at least 2:1. Thus, for example, if the input source is a 4 mm diameter cable, the input area is approximately 12.5 mm$^2$ and thus the extraction area is preferably at least 25 mm$^2$. The exemplary embodiment seen in FIGS. 3A-3D illustrate an illumination element such as an optical waveguide having an input 138 cross-sectional area that is at least two times smaller than the light extraction area 127-131. Additionally, the light extraction surface is parallel to the rear surface of the waveguide. The rear surface is substantially flat and planar. Additionally, the cross-sectional thickness of the input is larger than the thickness of the extraction area in order to ensure that profile at the extraction area remains low. Light output from the extraction area is also balanced. The surface features can vary dimensionally from the proximal part of the extraction zone to the distal part of the extraction zone so that light output does not vary across the surface and is uniformly delivered to the surgical field. For example each surface feature may include a stair step structure having a step face and a ramp face. An angle is disposed therebetween. The length of the step face or the ramp face may change between various stair steps in order to provide uniform illumination. Thus, the angle between the step face and ramp face may change between different stair steps in the extraction area. Additional details on the optical waveguide in FIG. 3 are disclosed in U.S. Pat. No. 8,088,066; the entire contents of which are incorporated herein by reference.

Figure 4:
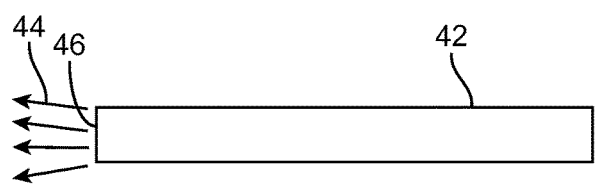
FIG. 4 illustrates an illumination element with a blunt distal tip.
Figure 5:
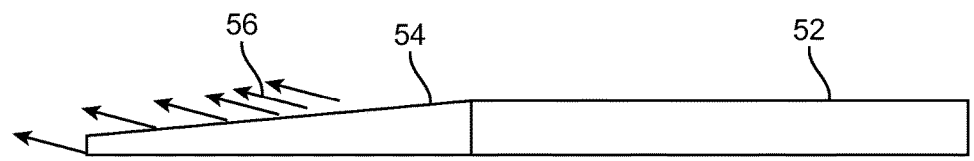
FIG. 5 illustrates an illumination element with a tapered tip.
Figure 6:
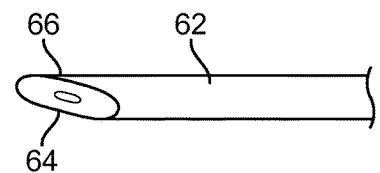
FIG. 6 illustrates a perspective view of an illumination element with a tapered tip.

FIG. 4 illustrates a typical illumination element such as waveguide 42 having a blunt distal end 46 that is orthogonal to the longitudinal axis of the waveguide 42. Light 44 travels through the waveguide and exits the distal end 46. Thus, the energy density is distributed over the surface area of the distal end 46. Other waveguides may have surface features such as microstructures on an outer surface to extract light laterally from the waveguide, as seen in FIG. 3. This allows the energy density to be distributed over a larger surface area. Using a tapered surface as seen in FIG. 5 allows an even larger surface area to created for light delivery, thereby further decreasing energy density. In FIG. 5, the illumination element is a waveguide 52 including a tapered tip 54 from which the light 56 is delivered. The tapered surface creates a larger surface area than that provided by a flat horizontal planar surface. FIG. 6 illustrates a perspective view of the tapered distal tip 64 of waveguide 62 with a flat and oval shaped 66 surface area for delivering the light. The ratios of input cross-sectional area and output cross-sectional area may be applied to any of the embodiments of illumination elements disclosed herein.

FIGS. 18A-18B illustrate how the surface area of a tapered surface may further be increased. FIG. 18A illustrates the surface area for light extraction in a simple tapered illumination element such as a waveguide. In FIG. 18B, the surface area for light extraction has been increased by adding stair stepped facets on the ramp, thereby adding additional surface area. The angle Θ is still preferably a maximum of 30 degrees in order to have at least a doubling of the area relative to the input cross-sectional area.

Output zones 127, 128, 129, 130 and 131 have similar configurations with different dimensions. Referring to the detailed view of FIGS. 3A-3C, the characteristics of output zone 127 are illustrated. Each output zone is formed of parallel prism shapes with a primary surface or facet such a primary facet 140 with a length 140L and a secondary surface or facet such as secondary facet 142 having a length 142L. The facets are oriented relative to plane 143 which is parallel to and maintained at a thickness or depth 144 from rear surface 145. In the illustrated configuration, all output zones have the same depth 144 from the rear surface.

The primary facets of each output zone are formed at a primary angle 146 from plane 143. Secondary facets such as facet 142 form a secondary angle 147 relative to primary facets such as primary facet 140. In the illustrated configuration, output zone 127 has primary facet 140 with a length 140L of 0.45 mm at primary angle of 27° and secondary facet 142 with a length 142L of 0.23 mm at secondary angle 88°. Output zone 128 has primary facet 140 with a length 140L of 0.55 mm at primary angle of 26° and secondary facet 142 with a length 142L of 0.24 mm at secondary angle 66°. Output zone 129 has primary facet 140 with a length 140L of 0.53 mm at primary angle of 20° and secondary facet 142 with a length 142L of 0.18 mm at secondary angle 72°. Output zone 130 has primary facet 140 with a length 140L of 0.55 mm at primary angle of 26° and secondary facet 142 with a length 142L of 0.24 mm at secondary angle 66°. Output zone 131 has primary facet 140 with a length 140L of 0.54 mm at primary angle of 27° and secondary facet 142 with a length 142L of 0.24 mm at secondary angle 68°.

Output end 133 is the final active zone in the illumination blade and is illustrated in detail in FIGS. 3A-3C. Rear reflector 148 forms angle 149 relative to front surface 150. Front surface 150 is parallel to rear surface 145. Terminal facet 151 forms angle 152 relative to front surface 150. In the illustrated configuration, angle 149 is 32° and angle 152 is 95°.

Figure 7:
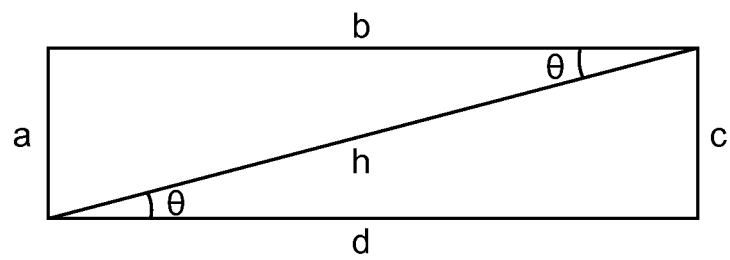
FIG. 7 illustrates increased surface area of a tapered tip relative to a flat horizontal tip.
Figure 16:
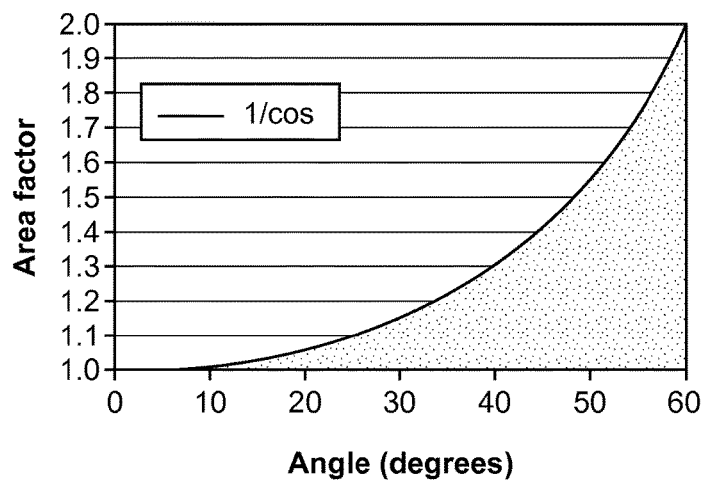
FIG. 16 illustrates the relationship between surface area and taper angle.

FIG. 16 illustrates the relationship between light output surface area and the taper angle. The angle in FIG. 16 is graphed as 90−Θ, where Θ is measured between the tapered surface and the flat planar back surface. FIG. 16 clearly shows that surface area increases with taper angle. FIG. 7 illustrates why a tapered surface provides a larger surface area compared to a flat planer horizontal surface. A flat planar illumination element such as a waveguide tip is defined by a-b-c-d, and light exits either surface a or surface b. Clearly surface b has a larger surface area than surface a. However, if a tapered tip is formed on the waveguide defined by c-d-h thereby forming a beveled tip, then the surface h becomes the extraction area, and has a length that can be calculated using basic trigonometry. Thus, $$h = c/\sin\Theta, \text{ or}$$

$$h = d/\cos\Theta$$

Since d=b, it is clear that h is longer than b when Θ is greater than zero degrees, thus the tapered tip provides a larger area for light extraction and delivery. Therefore the energy density is lower with a tapered tip relative to a flat planar vertical tip such as when light exits the distal-most face of a fiber. Similar calculations can be used to determine that the taper angle must be a maximum of 30 degrees (relative to the horizontal surface b or d) in order to create a surface that has a surface area at least twice that of the input surface area. The smaller the angle Θ, the more gradual the ramp angle, therefore the longer the beveled tip will be, increasing length and the corresponding extraction area.

FIG. 17A illustrates basic cone geometry, the cone having a base with radius r, a height h, and an outer surface s. Angle theta is defined between s and r. FIG. 17B illustrates the relationship between surface area and the angle Θ in the cone. Again, changing a conical taper changes the angle Θ which can have a significant impact on surface area. The conical taper may extend entirely around the circumference of the cone, or the taper may only be on a portion of the cone. The taper may symmetrical or non-symmetrical. The taper may be on one or more portions of the cone. Taper angles may be the same or different if more than one tapered portion exists. For example, a top portion of the cone may be tapered at one angle, and a bottom portion of the cone may be tapered at another angle. In an alternative embodiment, a top portion of the cone may have a taper angle and the bottom portion of the cone may be missing altogether.

Figure 8:
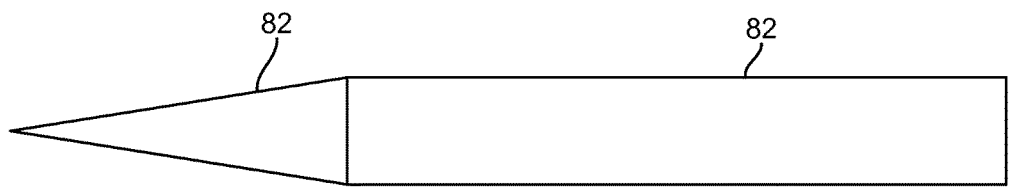
FIG. 8 illustrates an illumination element having a conically tapered tip.

FIG. 8 illustrates another means for reducing profile and creating a larger light extraction area by forming a conical taper 82 on the distal section of the illumination element, here a waveguide 82 instead of the flat taper previously described above. The cone may partially or completely surround the surgical instrument. Exemplary use of this includes an illuminated suction device that is completely formed from waveguide material. A central hollow bore (not illustrated) in the waveguide serves as a suction channel and allows suction to be applied without requiring a separate suction tube.

Figure 9:
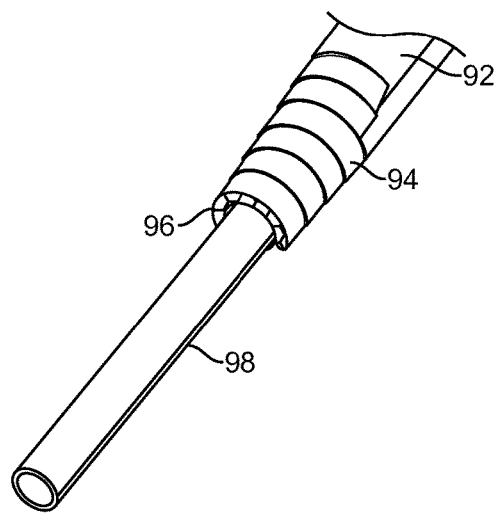
FIG. 9 illustrates still another exemplary embodiment of an illumination element with increased light extraction surface area.

FIG. 9 shows another embodiment of an illuminated surgical instrument having an increased light extraction surface area for controlling heat in the device. An illumination element such as an optical waveguide 92 is coupled to a suction tube 98. The waveguide 92 has a tapered region that tapers into different planes 94, thereby forming multiple stair steps or terraces. The planes may be the same or different. This design allows a long taper on the top and a shorter taper on the sides to create a more tailored light extraction mechanism. This creates the desired larger surface area for light extraction, as well as helps to keep the profile minimized. Surface features such as microstructures may be disposed on the tapered region to help extract and direct light from the optical waveguide. The surface features may be flat such as prisms, or other planar facet features, or the surface features may be radiused to further control the light being extracted from the waveguide. The surface features may be uniform or they may be each unique in order to extract and deliver the light as required by the application. Any combination of surface features may be used, such as lenslets 96 on the distal-most tip of the waveguide. The lenslets may overlap with one another so that light projected therefrom onto the surgical field also overlaps thereby providing more uniform illumination of the surgical field. This embodiment with a suction tube is not intended to be limiting and one of skill in the art appreciates that an illumination element may be coupled to any number of other surgical handheld instruments. Therefore, in still other embodiments, an illumination element may be coupled to any number of other handheld surgical instruments such as retractors, probes, electrosurgery instruments, a camera or other sensor instruments, etc.

Figure 10:
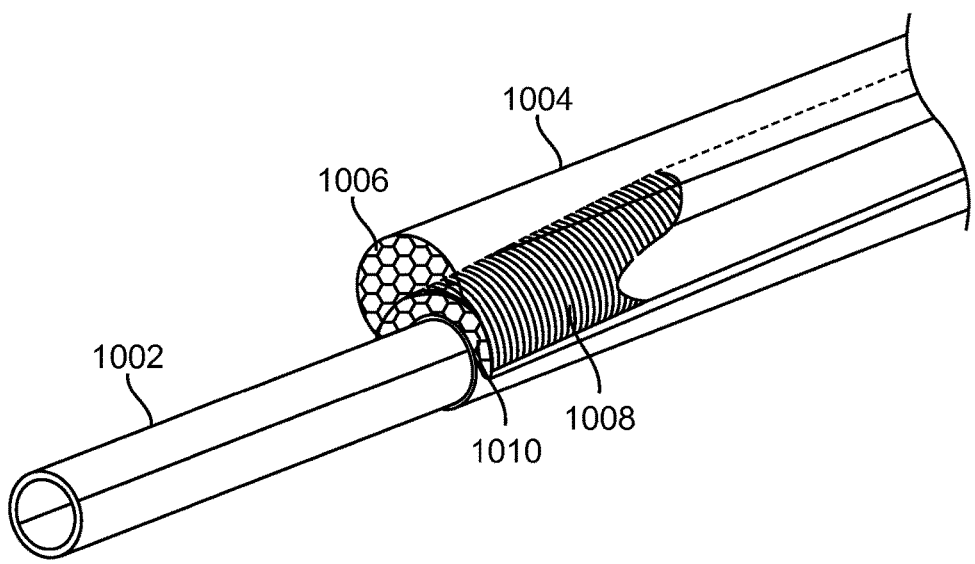
FIG. 10 illustrates a typical illumination element and a tapered tip illumination element disposed over a suction tube.

FIG. 10 illustrates a comparison between a typical illuminated suction instrument and one with a tapered multi-plane tip such as previously discussed in FIG. 9. The suction tube 1002 has a typical illumination element such as a waveguide 1004 disposed thereover and has lenslets 1006 on the distal tip of the waveguide. This view is transposed over the tapered tip waveguide having tapers into multiple planes 1008 and lenslets 1010 on the distal tip. It is clear that the improved waveguide has greater surface area and lower profile than the typical waveguide. Therefore, the improved waveguide will have lower energy density and control heat more effectively, and will not obstruct the surgical field as much as the typical illumination element or waveguide. Optical cladding may be disposed between the waveguide and the suction tube in order to prevent light loss from the waveguide. The index of refraction of the optical cladding is preferably in the range from 1 to 1.5. For example, cladding may be a layer of air over the waveguide (index of refraction 1), or various other polymers such as FEP heat shrink (fluorinated ethylene propylene) may be used. Other cladding materials may also be used. The thickness of the cladding is dependent on the material. For example, for some cladding, a cladding thickness of about 5 µm will result in only about 1% light loss, while thinner cladding coatings of 100 nm can result in up to 90% loss. The embodiment in FIG. 10 illustrates a suction tube combined with an illumination element such as an optical waveguide, however one of skill in the art will appreciate that the surgical instrument may be any other surgical instrument including a retractor blade, or other instruments described elsewhere in this specification. Cladding may be used in any of the embodiments disclosed in this specification.

In alternative embodiments, the illumination element may be a waveguide that may be a stand-alone device without coupling the waveguide to a surgical instrument. Thus, the waveguide may be used solely for illuminating the surgical field, or other work space. In still other embodiments, the illuminated suction device illustrated in FIGS. 9 and 10 may have a removable suction tube, thus the device may be used solely to illuminate, or the device may be used with the suction tube as an illuminated suction tube. Various diameters of suction tube may be provided in order to allow different fringe size suction. In still other embodiments, the illumination element may be coupled to any number of to other surgical instruments including but not limited to those disclosed in this specification.

Figure 11A:
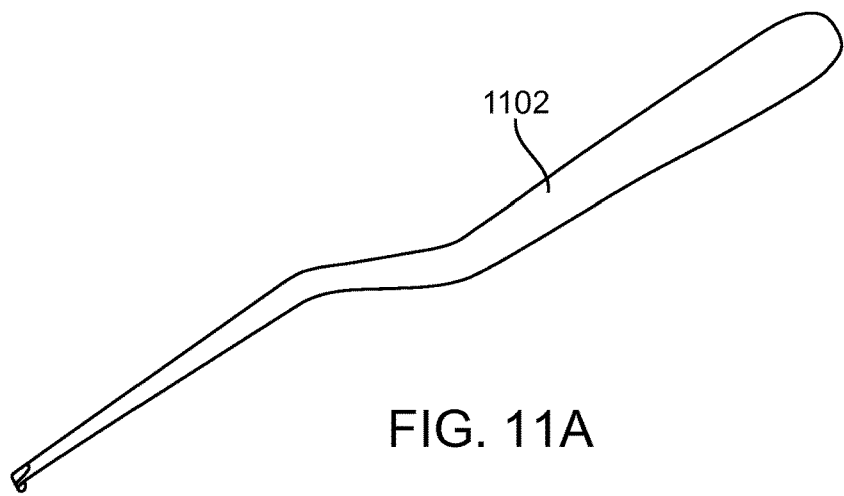
FIGS. 11A-11B illustrate other surgical instruments and tips.
Figure 11B:
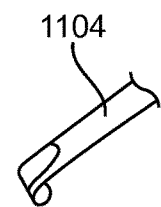
Figure 12:
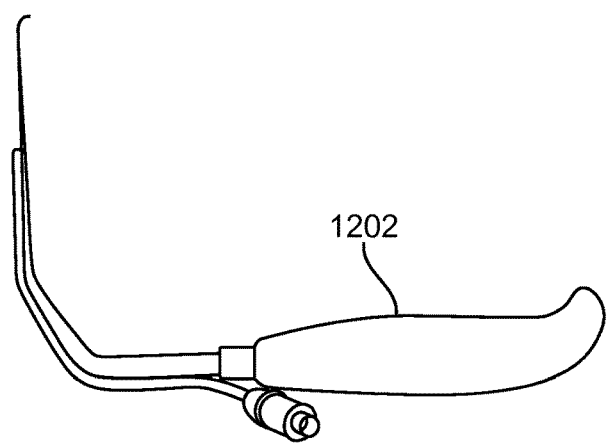
FIG. 12 illustrates still other surgical instruments and tips.

As previously discussed above, the optical waveguide may be used alone, or may be coupled to any surgical instrument to illuminate the surgical field during use of the instrument. Retractor blades and suction tubes are included in the preferred embodiments. Other surgical instruments which may be coupled to an illumination element such as an optical waveguide include but are not limited to such as probes, sensors, imaging elements such as video or other cameras, electrosurgical instruments, navigation instruments, neuro-monitoring instruments, etc. Other surgical instruments include nerve root retractors 1102 as seen in FIGS. 11A-11B having removable tips 1104, or coupled to a nerve root retractor coupled to a handle 1202 in FIG. 12 which clearly shows the profile issues as well as thermal hazard created because all of the light is extracted from the small tip.

Figure 13A:
FIGS. 13A-13D illustrate various embodiments of a surgical instrument with various tips.
Figure 13B:
Figure 13C:
Figure 13D:
Figure 14A:
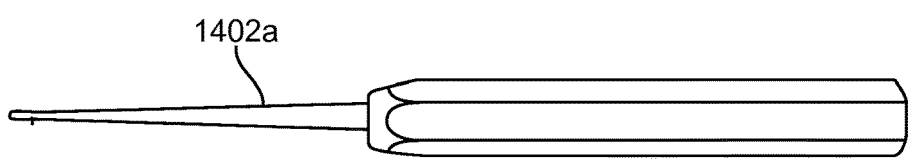
FIGS. 14A-14C illustrate other embodiments of a surgical instrument with various tips.
Figure 14B:
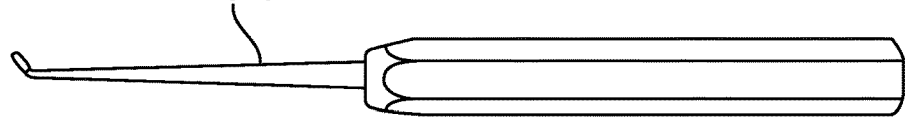
Figure 14C:
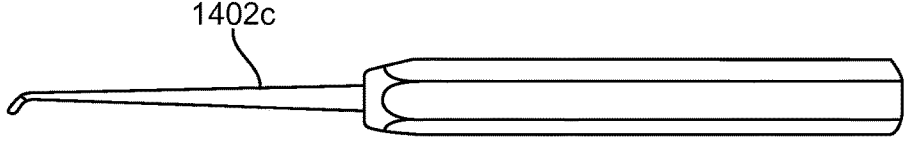

FIGS. 13A-13D illustrate other instruments that may be used with an illumination element like the optical waveguides described herein, such as ball tip probes having an upwardly bending tip 1302a in FIG. 13A, a rightwardly bending tip 1302b in FIG. 13B, a straight tip 1302c in FIG. 13C, and leftward bending tip 1302d in FIG. 13D. Also curettes seen in FIGS. 14A-14C may also be used with any of the illumination elements or optical waveguides described herein. FIG. 14A illustrates a straight tipped 1402a curette, FIG. 14B illustrates an angled tip 1402b curette, and FIG. 14C illustrates a reversed angle tip 1402 curette. In any of these surgical instruments, the illumination element or optical waveguide may be coupled to the entire surgical instrument, or simply the working end or tip of the surgical instrument may be coupled to the illumination element or optical waveguide.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An illumination element for illuminating a surgical field in a patient, said illumination element comprising:
  a light input section having an input area for inputting light into the illumination element;
  a light transmitting section, wherein the inputted light is transmitted through the light transmitting section, and wherein the light input section is optically coupled to a proximal section of the light transmitting section; and
  a light output section, wherein the light output section is adjacent a distal section of the light transmitting section, and wherein the light output section comprises a plurality of surface features increasing a surface area from which light is extracted relative to the input area, and
  wherein at least some of the plurality of surface features form one or more stair steps each having a primary facet and a secondary facet, the primary facet forming a primary angle relative to a plane parallel to a rear surface of the illumination element and the secondary facet forming a secondary angle relative to the primary facet, a sum of the primary and secondary angles being equal to or greater than 92 degrees and less than or equal to 127 degrees,
  wherein the surface area from which light is extracted is large enough to maintain an energy density at a level that prevents melting of the illumination element or burning of the patient, and wherein the surface area from which light is extracted has a low profile configured to avoid obstructing access to the surgical field and visualization thereof.

2. The illumination element of claim 1, wherein the light output section is tapered.

3. The illumination element of claim 1, wherein the light output section is conically tapered.

4. The illumination element of claim 1, wherein the light output section comprises an upper surface and a flat planar lower surface, and wherein the upper surface comprises a stepped surface area and is angled relative to the flat planer lower surface.

5. The illumination element of claim 4, wherein the upper surface forms an angle of 30 degrees or less relative to the flat planar lower surface.

6. The illumination element of claim 1, wherein the surface area from which light is extracted is at least twice a cross-sectional area of the light input section.

7. The illumination element of claim 1, wherein the surface area from which light is extracted is balanced so as to provide uniform light output therefrom.

8. The illumination element of claim 7, wherein the balanced light extraction area comprises surface features for extracting and directing the light.

9. The illumination element of claim 1, further comprising a cladding or a coating disposed over at least a section of the light input section, light transmitting section, or output section.

10. The illumination element of claim 9, wherein the cladding has an index of refraction in a range from about 1 to about 1.5.

11. The illumination element of claim 1, further comprising a surgical instrument coupled to the light input section, light transmitting section, or the light output section.

12. The illumination element of claim 11, wherein the surgical instrument comprises a suction tube or a surgical retractor blade.

13. The illumination element of claim 12, wherein the surgical instrument is a suction tube, and wherein the suction tube comprises interchangeably sized tips.

14. The illumination element of claim 11, wherein the surgical instrument comprises interchangeable instrument tips.

15. The illumination element of claim 1, wherein the illumination element comprises an optical waveguide.

16. The illumination element of claim 1, wherein the inputted light is transmitted through the light transmitting section by total internal reflection (TIR).

17. The illumination element of claim 1, wherein the light output section is formed of a single piece of light-transmitting material.

18. The illumination element of claim 1, wherein the light output section comprises a plurality of circumferential steps disposed thereon.

19. The illumination element of claim 1, wherein the light exits the light output section laterally.

20. The illumination element of claim 1, wherein the plurality of surface features comprises a plurality of stair steps, each stair step comprising a step face and a ramp face with an angle therebetween, wherein the angle in a first stair step is different from the angle in a second stair step.

21. The illumination element of claim 1, wherein the illumination element is a non-fiber optic optical waveguide.

22. The illumination element of claim 1, wherein energy density at the illumination input is higher than an energy density at the surface area where light is extracted from the illumination element.

* * * * *